(12) United States Patent
Salem, Jr.

(10) Patent No.: US 7,569,038 B1
(45) Date of Patent: Aug. 4, 2009

(54) DISPOSABLE DIAPER WITH ATTACHED WASTE BAG

(76) Inventor: Bernard Louis Salem, Jr., 69773 Sunset Heights, Bridgeport, OH (US) 43912

( * ) Notice: Subject to any disclaimer, the term of this patent is extended or adjusted under 35 U.S.C. 154(b) by 0 days.

(21) Appl. No.: 11/283,371

(22) Filed: Nov. 21, 2005

(51) Int. Cl.
*A61F 13/15* (2006.01)
(52) U.S. Cl. .............................. 604/385.13; 604/385.19; 604/385.01; 604/385.06; 604/385.02
(58) Field of Classification Search ............. 604/385.13, 604/385.19, 385.01, 385.06, 385.02
See application file for complete search history.

(56) References Cited

U.S. PATENT DOCUMENTS

| | | | |
|---|---|---|---|
| 4,604,096 A | * | 8/1986 | Dean et al. ............. 604/385.13 |
| 5,304,158 A | | 4/1994 | Webb |
| 5,582,605 A | | 12/1996 | Lepie |
| 6,004,307 A | | 12/1999 | Colon et al. |
| 6,350,931 B1 | | 2/2002 | Martin |
| 6,454,748 B1 | | 9/2002 | Ives |

\* cited by examiner

*Primary Examiner*—Jacqueline F. Stephens
(74) *Attorney, Agent, or Firm*—John D. Gugliotta

(57) ABSTRACT

A disposable diaper is provided having at least one pocket or pouch for containing an attached waste bag. The waste bag has an upper end adapted for sealable closure. The disposable diaper includes an elongated slit which provides entry into an interior cavity that is adapted to contain an auxiliary waste bag. The disposable diaper is embellished with ornamentation, decorative patterns, and symbols so as to represent a particular theme.

13 Claims, 7 Drawing Sheets

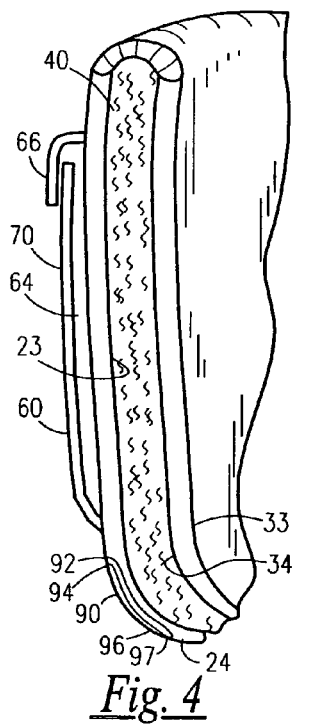
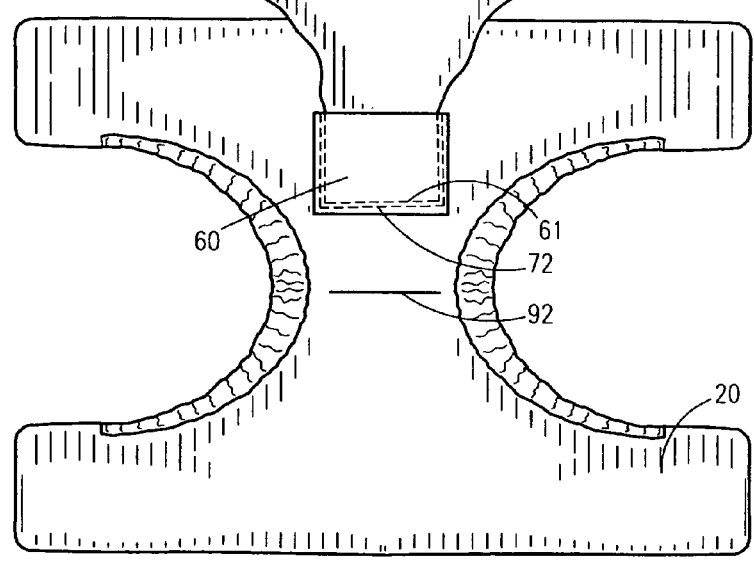
Fig. 4
Fig. 5

DISPOSABLE DIAPER WITH ATTACHED WASTE BAG

RELATED APPLICATIONS

The present invention was first described in Disclosure Document Number 581,671, filed on Jul. 8, 2005 under 35 U.S.C. §122, 37 C.F.R. §1.14, and MPEP §1706. There are no previously filed, nor currently any co-pending applications, anywhere in the world.

BACKGROUND OF THE INVENTION

1. Field of the Invention

The present invention relates generally to the field of diapers and, more particularly, to a disposable diaper with attached waste bag.

2. Description of the Related Art

The prior art discloses various disposable diaper devices having compartments or containers for storing baby care products such as lotions, creams, ointments, powder, wipes, and the like. However, the prior art does not describe a disposable diaper embellished with ornamentation having an attached waste bag adapted to sealably contain a soiled diaper.

Accordingly, a need has arisen for an ornamental, disposable diaper with attached waste bag. The development of the disposable diaper with attached waste bag fulfills this need.

A search of the prior art did not disclose any patents that read directly on the claims of the instant invention; however, the following references were considered related.

The following patents disclose various diaper packages and systems:

U.S. Pat. No. 5,582,605, issued in the name of Lepie;
U.S. Pat. No. 6,004,307, issued in the name of Colon et al.;
U.S. Pat. No. 6,454,748 B1, issued in the name of Ives; and
U.S. Pat. No. 5,304,158, issued in the name of Webb.

U.S. Pat. No. 6,350,931 B1, issued in the name of Martin discloses a tampon assembly with detachable cleansing towelette packet.

Consequently, a need has arisen for an ornamental, disposable diaper with attached waste bag, wherein waste bag has an upper end adapted for sealable closure, thereby preventing escape of counter offensive odor-causing bacteria and germs emitted by soiled diaper once stored within bag.

SUMMARY OF THE INVENTION

Therefore, it is an object of the present invention to provide a disposable diaper with attached waste bag.

It is another object of the present invention to provide a disposable diaper having at least one pocket or pouch integrally formed on diaper structure for containing the attached waste bag.

It is another object of the present invention to provide an attached waste bag having an upper end adapted for sealable closure.

It is another object of the present invention to provide a disposable diaper with an attached waste bag, wherein waste bag has a volume suitable for sealably containing a soiled diaper.

It is another object of the present invention to provide a disposable diaper having an elongated slit which provides entry into an interior cavity that is adapted to contain an auxiliary waste bag.

It is another object of the present invention to provide disposable diapers with attached waste bags which are independently embellished with ornamentation, decorative patterns, colors, indicia, phrases, markings, symbols, or the like, such that each ornamental diaper represents a particular theme.

Briefly described according to one embodiment of the present invention, a disposable diaper with attached waste bag is provided and comprises a diaper structure having an exterior layer. The exterior layer has in interior side and an exterior side and a generally horizontal upper edge for comfortable positioning around a baby.

The diaper also includes an interior layer having an interior side and an exterior side and a generally horizontal upper edge for comfortable positioning around a baby.

The diaper further comprises an intermediate layer between exterior layer and interior layer. The intermediate layer extends horizontally and vertically for the majority of the extent of exterior layer and interior layer. The exterior layer and interior layer are heat sealed or otherwise secured together in face-to-face relationship between which intermediate layer is securably sandwiched. Exterior layer and interior layer include arcuate-shaped voids being horizontally opposed and which form leg holes upon positioning of diaper around baby.

Horizontal upper edge of exterior layer and horizontal upper edge of interior layer include vertical edges which extend downwardly from each respective horizontal upper edge to an upper extent of leg holes. The vertical edges of interior layer are provided with an attachment means along the interior side thereof for securing exterior layer and interior layer on baby.

At least one pocket or pouch is integrally formed on diaper structure for containing an attached waste bag. The waste bag has a bottom portion suitably sealed and secured in the interior of pocket to a bottom thereof. The waste bag is folded in a manner allowing for its compact storage within pocket until waste bag access is required. The waste bag has an open, upper end providing passage into an interior thereof. The upper end of waste bag is adapted for sealable closure.

An elongated slit is formed about the diaper structure. The slit extends horizontally below pocket and between leg holes. The slit provides entry into an interior cavity which is adapted to contain an auxiliary waste bag.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 4 is a cross-sectional view taken along line IV-IV of FIG. 3, according to the preferred embodiment of the present invention;

FIG. 5 illustrates the waste bag shown deployed from the pocket, according to the preferred embodiment of the present invention;

DESCRIPTION OF THE PREFERRED EMBODIMENT

1. Detailed Description of the Figures

Figure 1:
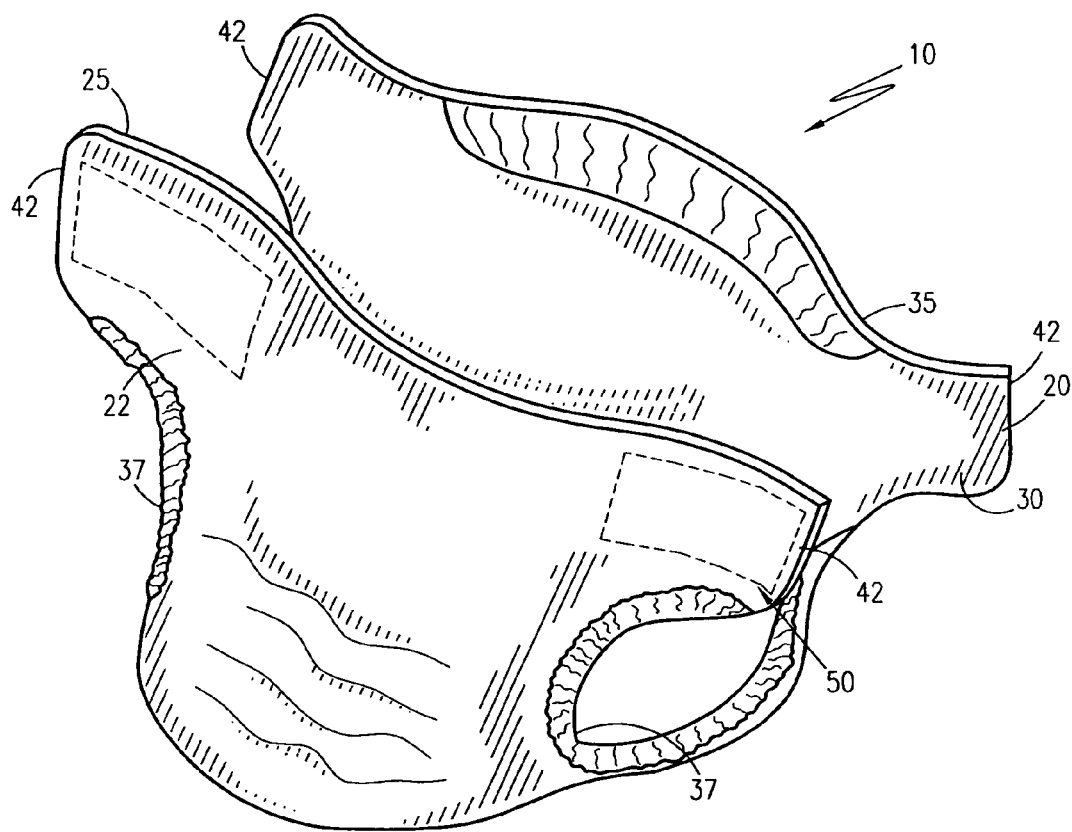
FIG. 1 is a perspective view of a disposable diaper with attached waste bag, according to the preferred embodiment of the present invention.
Figure 2:
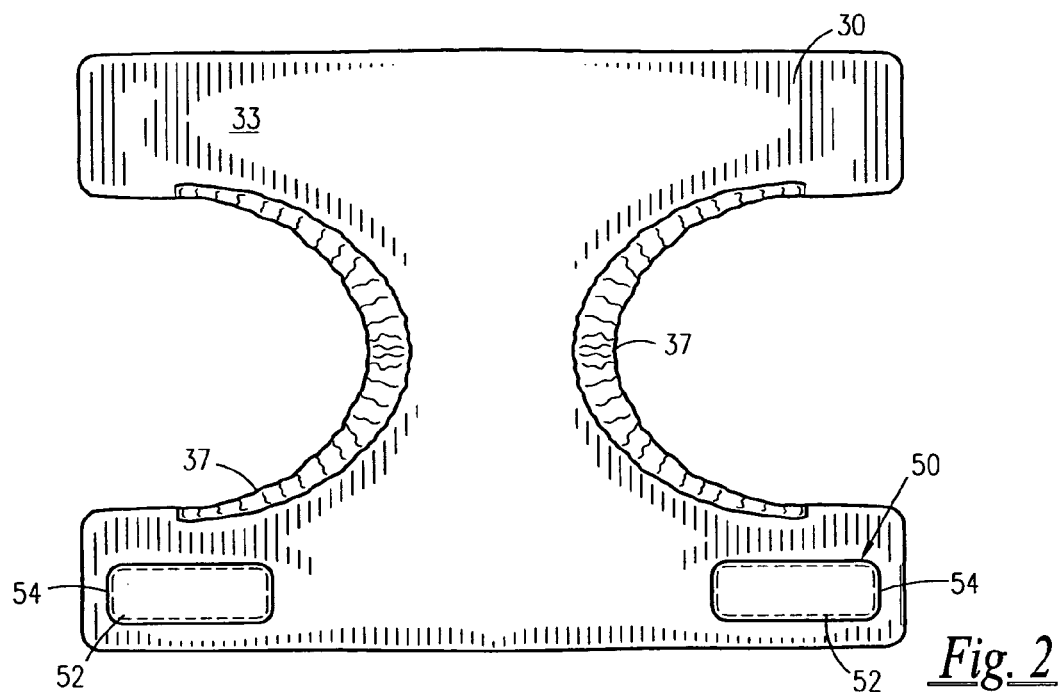
FIG. 2 is a top plan view thereof.
Figure 3:
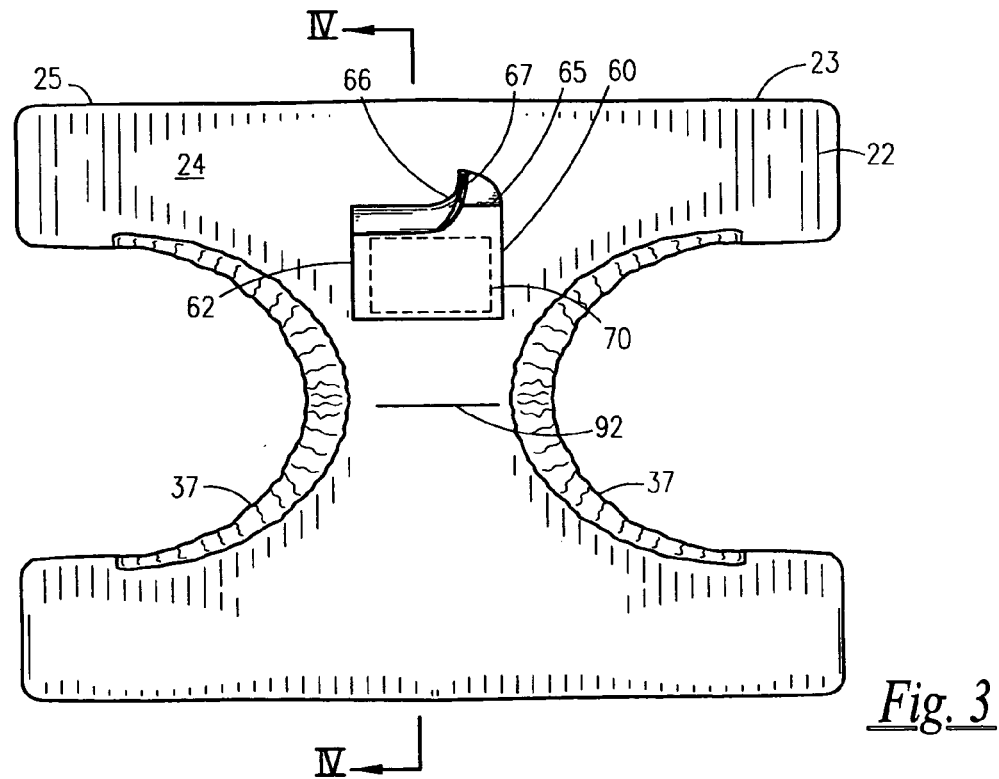
FIG. 3 is a bottom plan view thereof.

Referring now to FIGS. 1-4, a disposable diaper with attached waste bag 10 is shown, according to the present invention, comprised of a diaper structure 20 having an exterior layer 22. The exterior layer 22 is preferably fabricated of a flexible, liquid impervious material. The exterior layer 22 has in interior side 23 and an exterior side 24 and a generally horizontal upper edge 25 for comfortable positioning around a baby (not shown).

The diaper 10 also includes an interior layer 30, preferably fabricated of a flexible, liquid absorbent material. The interior layer 30 has an interior side 33 and an exterior side 34 and a generally horizontal upper edge 35 for comfortable positioning around a baby.

The diaper 10 further comprises an intermediate layer 40 between exterior layer 22 and interior layer 30, as shown in FIG. 4. The intermediate layer 40 extends horizontally and vertically for the majority of the extent of exterior layer 22 and interior layer 30. The intermediate layer 40 is constructed of a flexible, absorbent material.

The exterior layer 22 and interior layer 30 are heat sealed or otherwise secured together in face-to-face relationship between which intermediate layer 40 is securably sandwiched.

Exterior layer 22 and interior layer 30 include arcuate-shaped voids being horizontally opposed and which form leg holes 37 upon positioning of diaper 10 around baby. It is envisioned that diaper structure 20 is formed of a biodegradable fabrication material.

Horizontal upper edge 25 of exterior layer 22 and horizontal upper edge 35 of interior layer 30 include vertical edges 42 which extend downwardly from each respective horizontal upper edge 25, 35 to an upper extent of leg holes 37. The vertical edges 42 of interior layer 30 are provided with an attachment means 50 along the interior side 33 thereof for securing exterior layer 22 and interior layer 30 on baby. Attachment means 50 includes but is not limited to adhesive strips 52 and hook and loop fasteners. A removable cover 54 is disposed over the adhesive strips 52 until exposure of strips 52 is required. In the event hook and loop fasteners are utilized, the hook portion is suitably secured along the interior side 33 of interior layer 30 at vertical edges 42 and the loop portion is suitably secured along the exterior side 24 of exterior layer 22 at vertical edges 42.

Referring now to FIGS. 3-6, at least one pocket 60 or pouch is integrally formed on diaper structure 20 for containing an attached waste bag 70. Extending between leg holes 37 of the exterior side 24 of exterior layer 22 is a flexible layer of sheeting 62 forming pocket 60 having an interior 64. The pocket 60 is open at one end thereof and otherwise sealed about a periphery thereof to exterior side 24 of exterior layer 22. The pocket opening 65 includes a flap 66 with an adhesive strip 67 provided along an underside thereof to facilitate temporary closure of pocket opening 65.

Referring now to FIGS. 3-7, the attached waste bag 70 affords important functional utility to the present invention.

The waste bag 70 is fabricated of a lightweight, flexible, liquid impervious material. The waste bag 70 has a bottom portion 72 suitably sealed and secured in the interior 64 of pocket 60 to a bottom 61 thereof. The waste bag 70 is folded in a manner allowing for its compact storage within pocket 60 until waste bag 70 access is required. The waste bag 70 has an open, upper end 71 providing passage into an interior thereof. The upper end 71 is adapted for sealable closure. The upper end 71 includes a suitable sealing means 73 such as an adhesive strip, release liner, lip and tape, or zip lock style sealing means peripherally aligning the outer upper end 71 and adapted for facilitating complete sealable closure of waste bag 70. In an unfolded position, the waste bag 70 defines a size adapted with a suitable volume to contain a soiled diaper therein.

Figure 6:
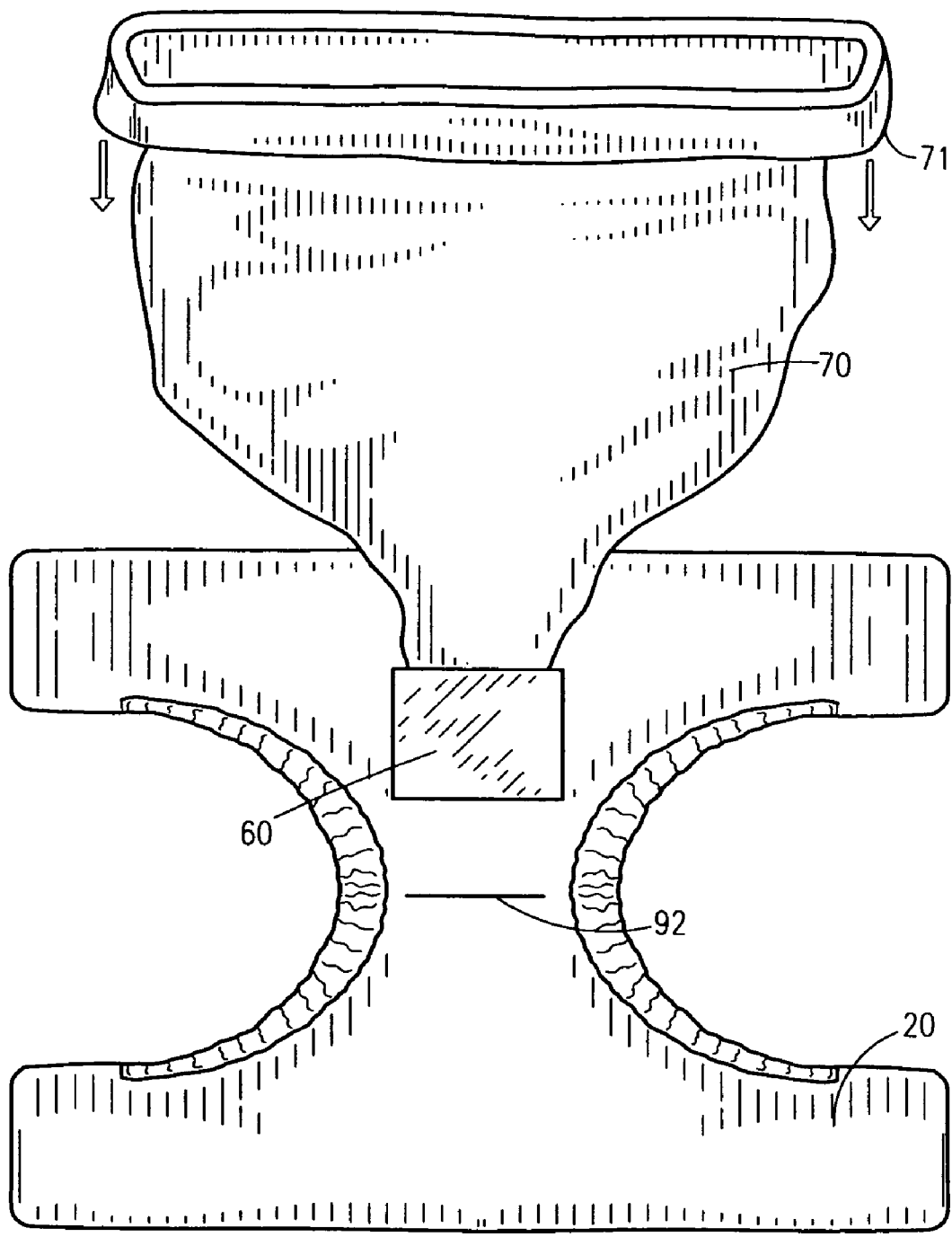
FIG. 6 illustrates the upper end of waste bag being reversed to an inside-out configuration, according to the preferred embodiment of the present invention.
Figure 7:
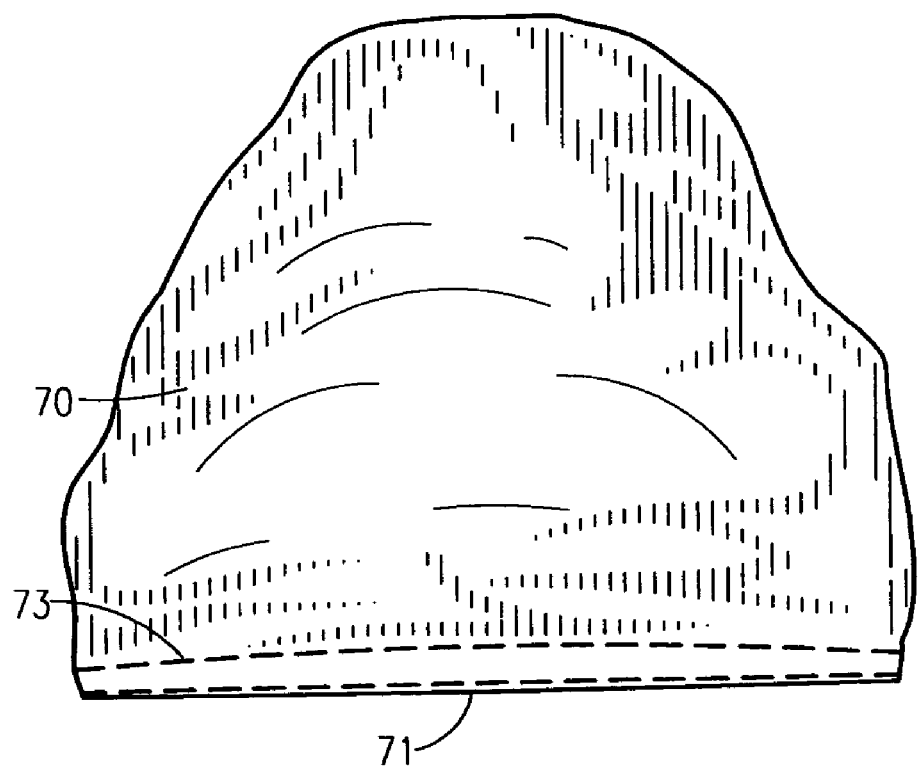
FIG. 7 illustrates a soiled diaper sealably contained within the waste bag, according to the preferred embodiment of the present invention.
Figure 8:
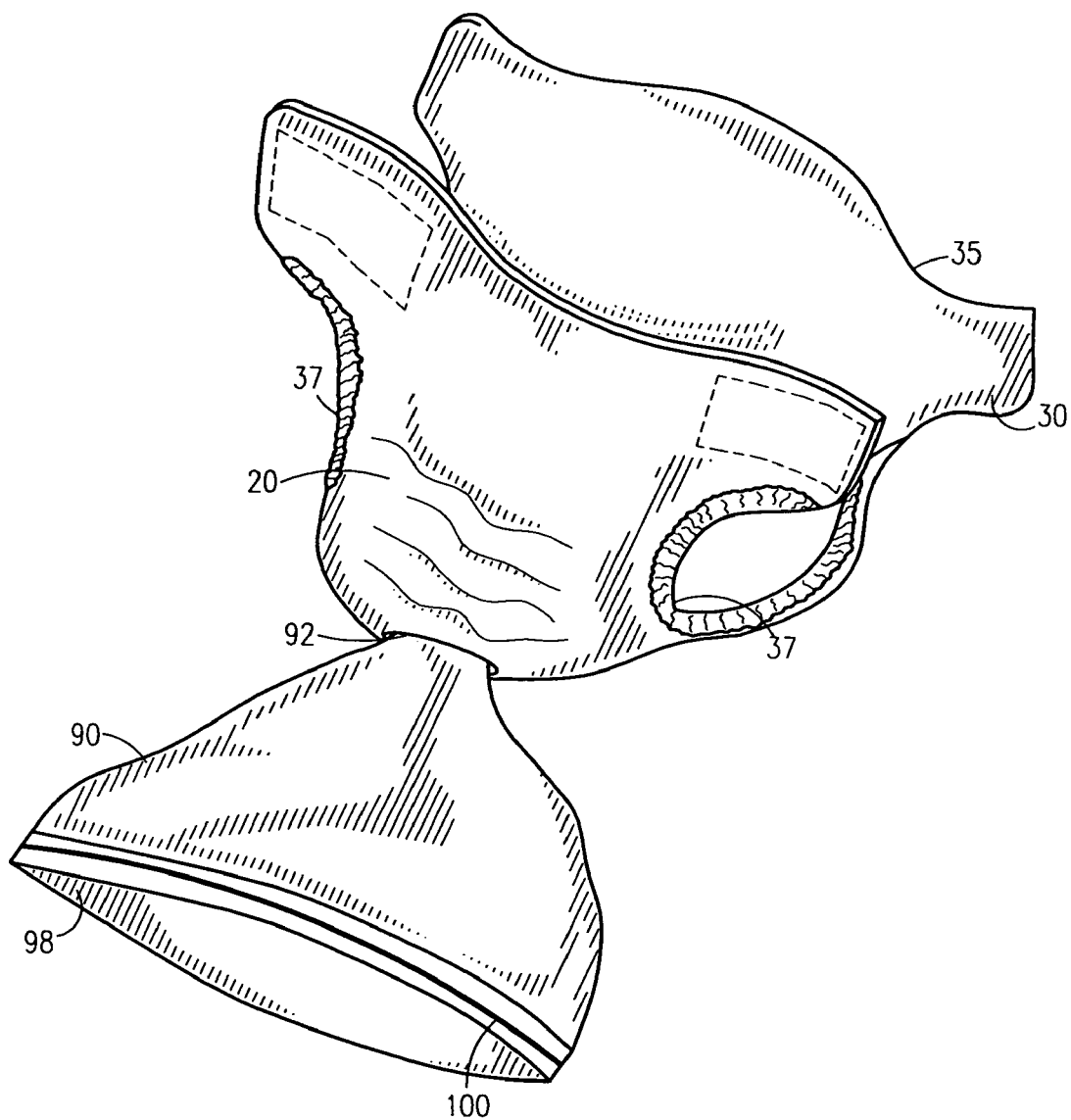
FIG. 8 illustrates the auxiliary waste bag shown deployed from the slit, according to the preferred embodiment of the present invention.
Figure 9:
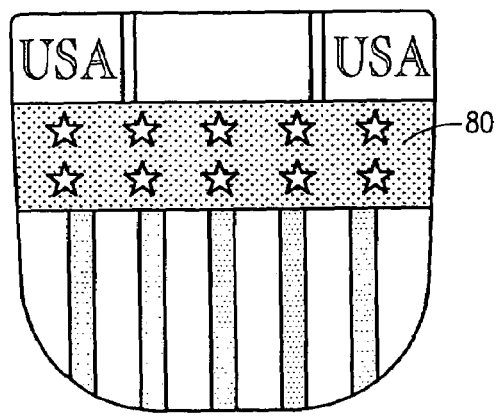
FIGS. 9-12 illustrate various disposable diapers with attached waste bags, each being individually adorned with distinctive ornamentation.
Figure 10:
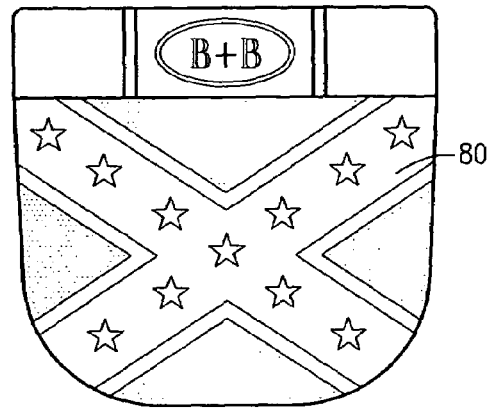
Figure 11:
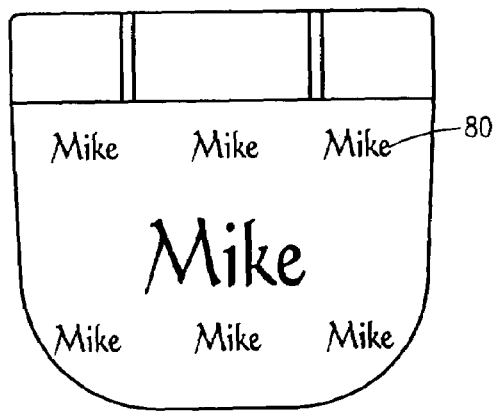
Figure 12:
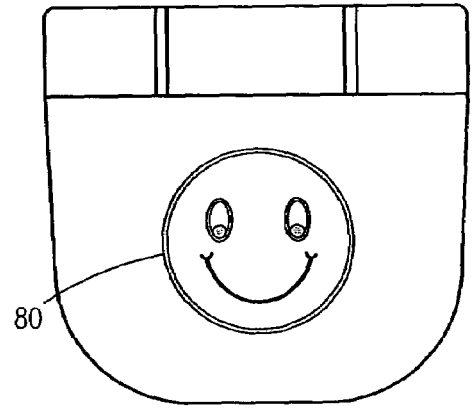

In order to easily dispose of a soiled diaper, user removes waste bag 70 from pocket 60, unfolds waste bag 70 and reverses or inverts the upper end 71 thereof in a manner whereupon waste bag 70 is turned inside out while simultaneously introducing soiled diaper within waste bag 70. After inserting soiled diaper within waste bag 70, user completely seals the upper end 71 thereof via sealing means 73, thereby preventing escape of counter offensive odor-causing bacteria and germs emitted by soiled diaper. The aforementioned method of diaper disposal is illustrated in FIGS. 5-7. Such method provides the user with a quick, easy, and efficient manner of disposing of a soiled diaper which creates less mess and odor.

Referring now to FIGS. 3-6 and 8, extending between leg holes 37 of the exterior side 24 of exterior layer 22, an elongated slit 92 is formed about the diaper structure 20. The slit 92 extends horizontally below pocket 60 and between leg holes 37. The slit 92 provides entry into an interior cavity 94 formed between exterior side 24 and interior side 23 of exterior layer 22. The interior cavity 94 is adapted to contain an auxiliary waste bag 90. The auxiliary waste bag 90 is fabricated of a lightweight, flexible, liquid impervious material. The auxiliary waste bag 90 has a bottom portion 96 suitably sealed and secured in the interior cavity 94 to a bottom 97 thereof. The auxiliary waste bag 90 is folded in a manner allowing for its compact storage within interior cavity 94 until auxiliary waste bag 90 access is required. The auxiliary waste bag 90 has an open, upper end 98 providing passage into an interior thereof. The upper end 98 is adapted for sealable closure. The upper end 98 includes a suitable sealing means 100 such as an adhesive strip, release liner, lip and tape, or zip lock style sealing means peripherally aligning the outer upper end 98 adapted for facilitating complete sealable closure of auxiliary waste bag 90. In an unfolded position, the auxiliary waste bag 90 defines a size adapted with a suitable volume to contain a soiled diaper therein.

In order to easily dispose of a soiled diaper, user removes auxiliary waste bag 90 from slit 92, unfolds auxiliary waste bag 90, reaches a hand into the interior of auxiliary waste bag 90 so as to use bag 90 as a glove, grabs diaper with bag 90 and makes an initial wipe of baby with diaper with hand still inserted within interior of bag 90. User next allows soiled diaper to collapse within auxiliary waste bag 90 and then follows the remaining aforesaid procedure described for disposing of a soiled diaper when utilizing waste bag 70 contained in pocket 60.

Referring now to FIGS. 9-12, a few examples are provided herein in order to illustrate that the exterior side 24 of the exterior layer 22 of each disposable diaper with attached waste bag 10 is individually adorned with distinctive ornamentation 80, decorative patterns, colors, indicia, phrases, markings, or symbols so as to represent a particular theme, wherein theme is broadly construed to comprise holidays and symbols therefor, sports, motor sports including but not limited to Nascar, IndyCar®, Formula 1™, open wheels, and the like, and sports symbols therefor, sports equipment and sports teams including but not limited to professional, college, high school, little league, and the like, personal names, musical notes, cities and states, flags, zodiac signs, wild life and exotic animals, domestic animals, aquatic life, prehistoric reptiles, cartoon characters, precious stones or gems, balloons, outer space objects such as stars, moon, planets and the like, traffic signs, skateboards, human skeletal structures, Southwestern cultural symbols and names such as "Aztec", geographical formations and objects, boats, airplanes, sailboats, super heroes, rainbow, cowboys and Indians, robots, farm equipment, dates in a calendar, indicia representing "hugs and kisses", i.e., "XOXOXOXO", musical genres, alcoholic beverage symbols and indicia therefor, phrases such as "heavy load", "keep back 30 feet", "smells like roses", "my dad owes child support", "tough guy", "I dare you", "change me", "I left you something", "who's my daddy", "I love my mommy", "I love my parents", "I'm in waste management", "toxic", "you want some", "great balls of fire", and "baby got back", and decorative patterns such as camouflage, tie-dye, clouds, waves, gingham, plaid, fruits, polka dots, flowers, stars and stripes, pin stripes, blue and white stars, black and white vertical strips, angel, flames, bull's eye, and blue jean. It is intended that each disposable diaper with attached waste bag 10 is independently embellished with a particular theme as described hereinabove, and thus purchaser will make diaper selection based upon a desired theme of choice.

2. Operation of the Preferred Embodiment

To use the present invention, user positions diaper structure 20 around a baby. Once diaper 20 has been soiled, thus requiring removal from baby, user removes waste bag 70 from pocket 60, unfolds waste bag 70 and reverses the upper end 71 thereof in a manner whereupon waste bag 70 is turned inside out while simultaneously introducing soiled diaper within waste bag 70. After inserting soiled diaper within waste bag 70, user completely seals the upper end 71 thereof via sealing means 73, thereby preventing escape of counter offensive odor-causing bacteria and germs emitted by soiled diaper.

The use of the present invention provides the user with a quick, easy, and efficient means of disposing of a soiled diaper which creates less mess and odor.

Therefore, the foregoing description is included to illustrate the operation of the preferred embodiment and is not meant to limit the scope of the invention. As one can envision, an individual skilled in the relevant art, in conjunction with the present teachings, would be capable of incorporating many minor modifications that are anticipated within this disclosure. The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be broadly limited only by the following Claims.

What is claimed is:
1. A disposable diaper comprising:
a diaper structure, said diaper structure comprises an exterior layer and an interior layer, said exterior layer has in interior side and an exterior side and a generally horizontal upper edge, said interior layer has an interior side and an exterior side and a generally horizontal upper edge, said exterior layer and said interior layer each include arcuate-shaped voids being horizontally opposed and which form leg holes upon positioning of said diaper structure around a baby;
an intermediate layer, said intermediate layer is sandwiched between said exterior layer and said interior layer, said intermediate layer extends horizontally and vertically for the majority of the extent of said exterior layer and said interior layer, and wherein said exterior layer and said interior layer are secured together in face-to-face relationship between which said intermediate layer is securably sandwiched;
at least one pocket or pouch being integrally formed on said exterior layer, said pocket or pouch comprises an opening that includes a flap with an adhesive strip provided along an underside thereof as means to facilitate temporary closure of said pocket opening, wherein said integral pocket or pouch contains an attached waste bag; and,
on auxiliary waste bag, said auxiliary waste bag resides in a folded condition within an interior cavity formed between said exterior side of said diaper and said interior side of said exterior side, said interior cavity is provided with entry therein via an elongated slit which extends between leg holes of said exterior side of said exterior layer, said elongated slit extends horizontally below said pocket and between said leg holes;
wherein said auxiliary waste bag has a bottom portion suitably sealed and secured in said interior cavity to a bottom of said interior cavity, said auxiliary waste bag has an open, upper end providing passage into an interior thereof, said open, upper end is adapted for scalable closure, and wherein said open, upper end includes a suitable sealing means peripherally aligning an outer portion of said open, upper end, said sealing means is adapted for facilitating complete scalable closure of said auxiliary waste bag, said auxiliary waste bag defines a size adapted with a suitable volume to contain a soiled diaper therein upon deployment of said auxiliary waste bag.

2. The disposable diaper of claim 1, wherein said integral pocket or pouch is formed of a flexible layer of sheeting, said pocket extends between said leg holes of said exterior side of said exterior layer, said pocket having an interior, said pocket is formed with perforation at one end so as to define a pocket opening which provides passage into said interior, and wherein said pocket is otherwise sealed about a periphery thereof to said exterior side of said exterior layer.

3. The disposable diaper of claim 1, wherein said waste bag has a bottom portion suitably sealed and secured in said interior of said pocket to a bottom of said pocket, said waste bag is folded in a manner allowing for its compact storage within said pocket until said waste bag access is required.

4. The disposable diaper of claim 3, wherein said waste bag has an open, upper end providing passage into an interior of said waste bag, said upper end includes a suitable sealing means peripherally aligning an outer portion thereof, said sealing means is adapted for facilitating complete sealable closure of said waste bag, said sealing means comprise:
an adhesive strip;

a release liner;

a lip and a tape; or, a zipper and a lock.

5. The disposable diaper of claim 1, wherein said diaper structure is constructed of a biodegradable material.

6. The disposable diaper of claim 1, wherein said exterior layer is fabricated of a flexible, liquid impervious material capable of being fused about the periphery of said integrally formed pocket or pouch, and further being capable of being perforated such as to form an opening of said pocket or pouch.

7. The disposable diaper of claim 1, wherein said interior layer is fabricated of a flexible, liquid absorbent material.

8. The disposable diaper of claim 1, wherein said intermediate layer is fabricated of a flexible, absorbent material.

9. The disposable diaper of claim 1, wherein said waste bag is fabricated of a lightweight, flexible liquid impervious material.

10. The disposable diaper of claim 9, wherein said auxiliary waste bag is fabricated of a lightweight, flexible, liquid impervious material.

11. The disposable diaper of claim 1, wherein said exterior side of said exterior layer of each said diaper structure is individually or independently adorned with distinctive ornamentation, decorative patterns, colors, indicia, phrases, markings, or symbols so as to represent a particular theme.

12. The disposable diaper of claim 11, wherein said theme is selected from the group comprising:

holidays and symbols therefor, sports, motor sports and sports symbols therefor, sports equipment and sports teams, personal names, musical notes, cities and states, flags, zodiac signs, wild life and exotic animals, domestic animals, aquatic life, prehistoric reptiles, cartoon characters, precious stones or gems, balloons, outer space objects, traffic signs, skateboards, human skeletal structures, Southwestern cultural symbols and names, geographical formations and objects, boats, airplanes, sailboats, super heroes, rainbow, cowboys and Indians, robots, farm equipment, dates in a calendar, indicia representing "hugs and kisses", musical genres, alcoholic beverage symbols and indicia therefor, phrases.

13. The disposable diaper of claim 1, further comprising an otherwise conventional baby wipe disposed within said at least one pocket or pouch.

\* \* \* \* \*